United States Patent [19]
Zeiser

[11] Patent Number: 4,842,515
[45] Date of Patent: Jun. 27, 1989

[54] SUPPORTING PLATE FOR A DENTAL MODEL AND METHOD OF MAKING A DENTAL MODEL

[76] Inventor: Manfred P. Zeiser, Im Wolfsgalgen 8, 7141 Schwieberdingen, Fed. Rep. of Germany

[21] Appl. No.: 44,979

[22] Filed: Apr. 30, 1987

[30] Foreign Application Priority Data

May 10, 1986 [DE] Fed. Rep. of Germany ....... 3615821

[51] Int. Cl.⁴ .............................................. A61C 19/00
[52] U.S. Cl. ...................................... 433/74; 433/34; 433/49
[58] Field of Search ...................... 433/34, 53, 60, 74, 433/213

[56] References Cited

U.S. PATENT DOCUMENTS

| | | | |
|---|---|---|---|
| 4,283,173 | 8/1981 | Browne et al. | 433/34 |
| 4,538,987 | 9/1985 | Weissman | 433/34 |
| 4,608,016 | 8/1986 | Zeiser | 433/74 |
| 4,708,648 | 11/1987 | Weissman | 433/34 |

Primary Examiner—Larry Jones
Attorney, Agent, or Firm—Michael J. Striker

[57] ABSTRACT

A supporting plate for a denture model includes a cheek-side portion and a tongue-side portion spaced from each other to define a groove therebetween and connected to each other by flexible pivotable webs so that the distance between those portions is changeable whereby an unavoidable expansion of a model material is compensated for by a change of the shape of the supporting plate.

45 Claims, 4 Drawing Sheets

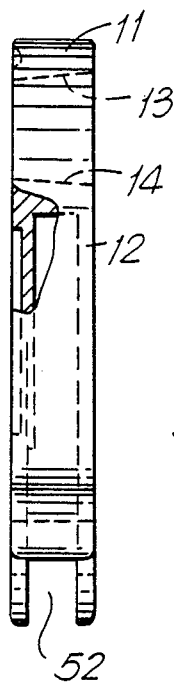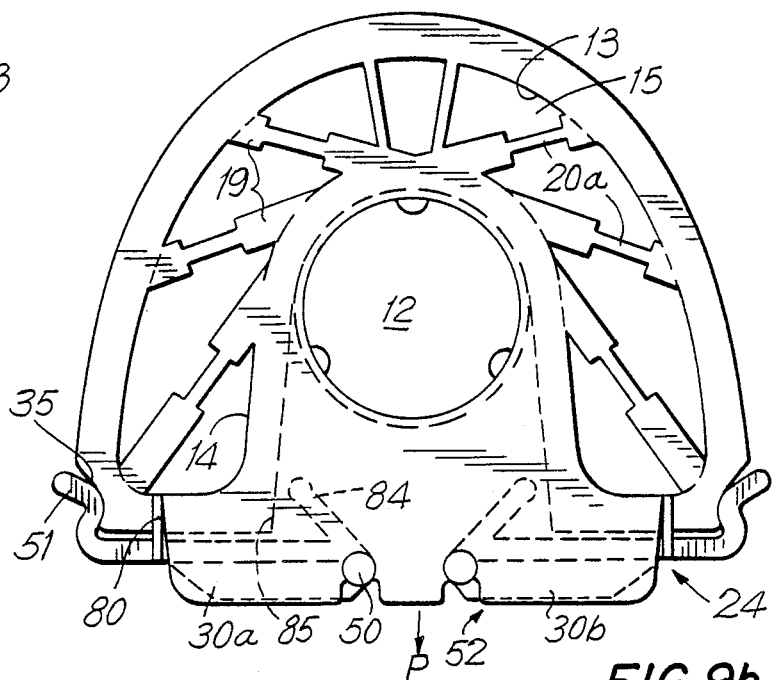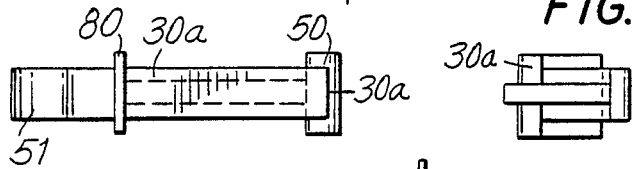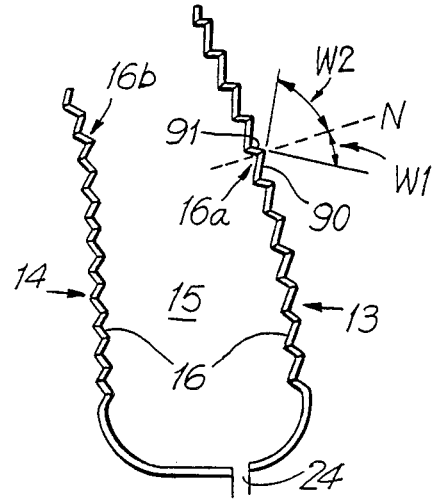

SUPPORTING PLATE FOR A DENTAL MODEL AND METHOD OF MAKING A DENTAL MODEL

BACKGROUND OF THE INVENTION

The present invention pertains in general to a device for making a denture mold which is utilized in dental techniques for making teeth prostheses. More specifically the invention relates to a supporting plate into which a prosthesis or model material to be hardened is filled.

Supporting plates for dental devices have been disclosed in applicant's U.S. Pat. Nos. 4,371,339 and 4,608,016.

A supporting plate comprising two portions has been disclosed, for example in DE-PS No. 28 56 963 corresponding to U.S. Pat. No. 4,283,173. One of the portions is a cheek-side portion and another is a tongue-side portion. These portions are connected to each other by a plurality of webs. These two portions have side walls facing each other and defining a groove of the shape of the dental arch and forming guiding surfaces for a model tooth stump. The portion of the supporting plate and the webs are made of one-piece from a rigid plastic. The distance between the opposing side walls of two portions is constant and unchangeable due to the webs which connect the side walls of the two portions of the supporting plate at the shortest distance.

Studies have shown that dental models manufactured with such supporting plates have not been sufficiently precise to meet the requirements of modern dental practice. Measurements by the microscopes have proven that with such dental models it has not been possible to set individual model teeth stumps, after the sawing up operation, back to the initial position in the supporting plate. Gypsum expands during its hardening whereby this expansion has a negative effect on the model in the direction transversal to the direction of elongation of the tooth arch while the expansion in the direction of elongation is compensated for by a saw clearance, particularly when the tooth arch is divided into many portions. By the expansion of individual tooth stumps transversely to the direction of elongation of the dental arch the distance between two guide surfaces is increased so that individual sawn portions or model tooth stumps can not be adjusted relative to each other in height in the groove which is conically widens in the known supporting plate, and the distance between the side walls limiting that groove remains unchanged due to the use of a formstable plastic, and is also smaller than the distance between the guide surfaces after the hardening of the model material.

To eliminate the disadvantage of an incorrect height relations between individual tooth stumps, the tooth stump has been often pressed into the groove with a substantial external effort whereby a slightly smaller expansion has been obtained at the front teeth region of the dental arch than at the back teeth area. This has caused a deformation of the model tooth stump which affected the precision of the denture model.

Moreover, with the use of conventional supporting plates, a play-free guidance of individual tooth stumps has been achievable so that a precise initial positioning or repositioning of individual tooth stumps was not ensured.

SUMMARY OF THE INVENTION

It is an object of the present invention to provide an improved supporting plate for making dental models and a method of manufacturing dental models.

It is another object of the invention to provide a supporting plate with which individual tooth stumps could be returned to their initial position after the sawing up operation.

These and other objects of the invention are attained by a supporting plate for a dental model for the preparation of dental prothesis parts, comprising a first tongue-side portion and a second cheek-side portion, both portions having walls which are to aligned with each other, said first and second portion defining therebetween a groove of a shape corresponding to the shape of a tooth arch and forming respective guiding surfaces for guiding a model tooth stump during the hardening of a model material, and at least one connection element for holding said second portion on said first portion, said connection element being formed so that it permits a change in a distance between a side wall of said second portion and a side wall of said first portion.

The invention is based on the knowledge that the expansion of the model material even with the use of rigid material for the supporting plates can not be avoided or limited. The invention is based on the principle that the shape of the supporting plate must be adjusted to the expansion of the model material. This is possible when one or many connecting elements between the portions of the supporting plates are formed so that the change in the distance between the walls of those portions is possible. According to the invention at least the side wall of one of the portions is made flexible.

Various modifications of this invention are possible.

The cheek-side portion can be subdivided into individual portions which would be guided or freely radially moved, by radially directed guide elements on the internal or tongue-side portion. Such a multi-part supporting plate is comparatively non-expensive in manufacture, but determines by additional abutments or the like the end positions of the adjustable portions of the supporting plate.

The connection element may be formed so that it elastically counteracts to increase of said distance between the side walls of said second and first portion. With such a modification the distance between the portions which is the width of the groove between the portions is continually increased with expansion of the model material so that an exact position of the side walls on the guide surfaces of the tooth stumps is obtained.

Spacer means may be provided to assure a smallest distance between said side walls.

The connection element may be simultaneously a spacer element.

The connection element may be formed by a web and is pivotable by an angle deviated from 90° on a side wall of each portion.

The difference between the webs of conventional supporting plates and those of this invention is that the web or webs are pivotable on the portion of the plate at the angle which is greater or smaller than 90°. The length of the web is also greater than the original minimal width of the groove between said portions. During the expansion of the model material this angle of extension of the web changes, which leads to enlargement of the groove width.

The web may be connected to the side wall of each portion by film hinges integral with said web. A predetermined position of the web is thus defined by the film hinge and the minimal distance between two portions of the plate is also defined.

The web may be formed of one-piece with said first and second portion and has an intermediate portion positioned in the middle between said second and first portion, said intermediate portion having a reduced cross-section, whereby flexibility of the web in the direction transverse to the direction of elongation of the tooth arch is obtained whereas the cheek-side portion of the plate remains sufficiently rigid.

A plurality of connection elements may be provided, said connection elements being formed by webs which are uniformly spaced from each other, at least one of said webs being directed towards a point which is positioned in the middle between two cutting teeth.

All the webs may be parallel to each other. A parallelogram-like arrangement may be realized. Such arrangement is particularly advantageous when the cheek-side portion is subdivided into many segments. The web arrangement may be formed according to the principle of the Nurenberg scissors.

The webs may be connected to each other by a reinforcing web extending in the middle between said second and first portion along said groove.

A material utilized for the webs has itself a required elasticity.

The webs may cover more than one half of a base surface of said groove.

It is ensured by suitable dimensioning and selection of a material of the webs that the elastic distance change between the facing side walls of said portions is obtained. Since a translatory displacement of the cheek-side wall superposes a determined rotation movement, projections are provided directly on the cheek-side wall and these movements are not obstructed.

A thin foil, which closes said groove before said groove is filled with model material, may be placed on said webs, said foil forming said base surfaces.

The supporting plate may further include locking means for elastically locking said first portion with said second portion with a sufficient clamping force.

The locking means may include at least one clasp which clamps free ends of said second portion with said first portion.

The locking means may include two clasps which clamp free ends of said second portion with said first portion, said two clasps being pivotally connected to each other.

The locking means may include a bolt connection which connects free ends of said second portion to said first portion.

The locking means may include two clasps which clamp free ends of said second portion and are pivotally connected to said first portion.

Said second portion may be divided in the region of front teeth into a plurality of parts connected to each other by a clamping tape extending about said second portion.

The clasps may be locked in both portions or in one of said portions.

The clasp may have two bridges and a cross-piece connecting said bridges to each other, said bridges engaging opposite base surfaces of said first and second portion and snugly closing said first and, second portion.

At least one of said portions may have a recess in which said two clasps are engaged.

The first portion may have said recess (52) in which said two clasps are engaged, said clasps being supported in said second portion in the direction transverse to said base surface.

Each clasp may have a projection which is engaged in a recess formed of a respective one of said portions.

Each clasp may have a plate portion provided with said projection, said plate extending substantially normal to elongation of said clasp and projecting into a play between said first and second portion and filling said play.

Each clasp may further have a resilient abutment which, affect the assembly of the clasp in a direction of elongation and a following pivoting to an operation position, makes a pivoting of the clasp backward to an assembly position difficult.

Said locking may be effected by a tub-shaped mold into which the supporting plate is directly insertable so that an outer wall of said second portion lies against a side wall of the mold.

The side walls of said first and second portion, which face toward each other may have ribs, wherein a cross-section of each rib on a side wall of said second portion differs from a cross-section of each rib on a side wall of said first portion, each rib having wall portions which include with a normal (N) to the side wall of said second portion a different angle (W1, W2), and an angle Wx between said normal and a wall portion directed towards a back teeth region is greater than an angle (W1) between said normal and wall portion.

Angle (W2) may be in the range between 50 and 60 deg. and angle (W1) is in the range between 25 and 35 deg.

The supporting plate may be made of plastic or mineral glass.

The objects of the invention are also attained by a method of making a dental model with the supporting plate, comprising the steps of filling a hardenable model material into said supporting plate the side walls of which during hardening of said material form guide surfaces on a guide abutment of a model tooth stump, wherein at least during a predetermined time interval while said material is hardened a deflection of a side wall of a portion of the supported plate is permitted.

The method of the invention further comprises the steps of locking said first and second portion to each other before and releasing said first portion from said second portion after solidifying of said material.

The model material can be also completely hardened in the supporting plate or removed therefrom after it has been solidified but not completely hardened.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 8 is a backside view of yet another embodiment;

FIG. 9a is a side view of the clasp;

FIG. 9b is a front view of the clasp of FIG. 9a;

FIG. 10 is a grooved portion, on enlarged scale;

FIG. 11 is a partial sectional view through the base plate of FIG. 8;

DETAILED DESCRIPTION OF THE PREFERRED EMBODIMENTS

Figure 1:
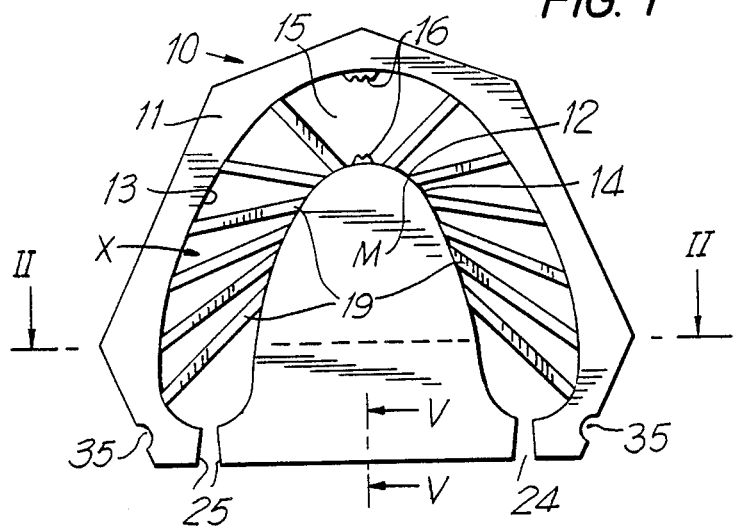
FIG. 1 is a plan view of the first embodiment of the base plate of the device for making a denture mold.

Referring now to the drawings in detail, FIG. 1 shows a supporting of plate 10 for an impression receiving member carrying a denture impression or dental model. Base plate 10 includes two portions 11 and 12 with side walls 13 and 14 which are laterally limited by a groove 15 adjusted to a dental arch. These side walls are provided in the known manner with projections and grooves 16a which for the sake of clarity are shown only partially. These side walls 13 and 14 form, during the hardening of the model material filling the groove 15, corresponding guide surfaces on the guiding abutments of individual model tooth stumps, whereby it is ensured by means of retensions 16 that these model tooth stumps sawn out from the dental arch can only later be placed back to the initial position in the groove or the supporting plate 10.

The cheek-side portion 11 of the base plate is connected with the tongue-side portion 12 by connection elements formed by narrow webs 19 which allow for a distance change between the cheek-side portion 11 and the tongue-side portion 12.

Figure 3:
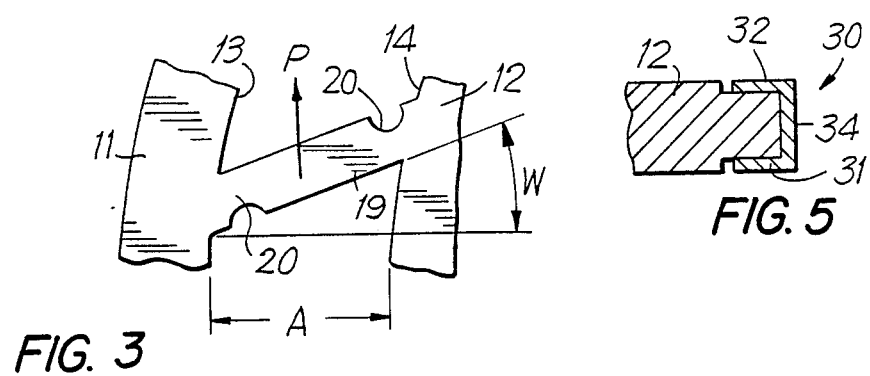
FIG. 3 is a detail X of FIG. 1.

As seen from FIGS. 1 and 3, webs 9 are inclined at the angle W less than 90° to the cheek-side portion 11 and tongue-side portion 12, and are formed integral or in one piece with these portions. Near the transition into the side walls 13 and 14, webs 19 have a reduced cross-section (FIG. 3) so as to form film hinges 20. These reductions in cross-sections are not shown in the plan views of the base plate for the sake of clarity. These cross-section reductions could be omitted when the webs have a very small cross-section and a suitable material is utilized.

Figure 2:
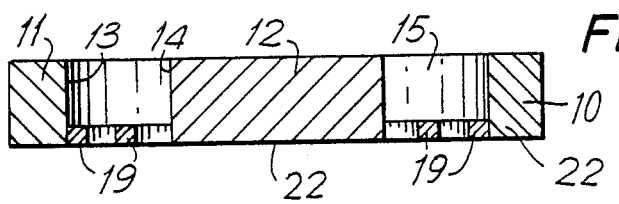
FIG. 2 is a sectional view taken on line 11—11 of FIG. 1.

In the embodiment of FIG. 1 all webs 19 are oriented towards a common point M which is positioned in the middle shortly behind both cutting teeth. FIG. 2 shows that these relatively thin-walled webs 19 are snugly closed with the lower base surfaces 22 of the both partions of the base plate, lying in one plane.

The base plate shown in FIG. 1 differs from the known base plate for the denture mold in that both portions of the base plate are not connected to each other in the region of the jaw teeth. Furthermore, a play or clearance 24 is at the right and the left side respectively, and regions 25 which lie laterally of each play 24 form, respectively on the cheek-side plate portion and the tongue-side plate portion abutments which can serve as spacer elements and define a minimial width of groove 15 or a minimial distance A between two side walls 13 and 14.

It is important for the present invention that due to the structure of the base plate 10 the cheek-side plate portion 11 or its side wall 13 can spring or yield outwardly. Thereby the minimial distance A is firstly adjusted by the orientation of webs 19 which also fulfil the function of the spacer elements.

If the model material, which fills the groove 15, expands the forces act transversely to the direction of elongation of the dental arch and the distance A between the side walls 13 and 14 is increased by these forces due to the pivoting of the webs 19 in the direction of arrow P, whereby webs 19 will act resiliently in opposition to the distance increase. The distance change is possible because angle W of the inclination of webs 19 can not change originally the groove 15 as known in the art but to bridge the shortest path. This change in the angle of inclination is possible due to the film hinge on the webs. The maximal distance between the side walls 13 and 14 is obtained when webs 19 extend at right angles to the side walls. Such a condition usually is not achieved.

Figure 4:
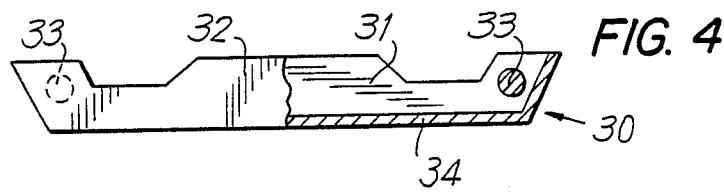
FIG. 4 is side view, partially in section, of a clasp.
Figure 5:
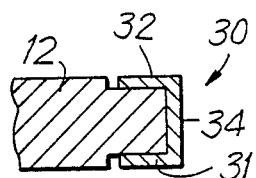
FIG. 5 is a partial sectional view taken on line V—V of FIG. 1, showing the base plate with the locked clasp.

Elasticity of the web connection is selected by a suitable dimensioning of the film hinge so that the base plate 10 or groove 15 can, during the expansion of the model material, be adjusted to the occuring change of the cross-section. Thereby a restoring force which is exerted by webs 19 after the deflection is not sufficient to reliably hold a model tooth stump inserted in groove 15. Therefore the locking between the cheek-side plate portion 11 and the tongue-side portion 12 is provided, which is shown in FIG. 4. The locking means is formed by a clasp 30 which has a U-shaped cross-section. Clasp 30 includes two spaced parallel cross-pieces or bridges 31 and 32 which near their ends are connected to each other by vertically projecting arresting or locking pins 33 and also by a cross web 34. Locking recesses 35 are formed at the free ends of the cheek-side plate portion 11; these locking recesses receive and arrest locking pins 33. As clearly seen from FIG. 5 the external surfaces of bridges 31 and 32 fit and overlap opposing base surfaces of the plate portions 11 and 12 and thereby serve for a two-side alignment or orientation to be snugly closed with the base surfaces of the plate portions 11, 12. If the clasp 30 with locking pins 33 is inserted into locking recesses 35 the clamping force of clasp 30 acts on the free ends of the cheek-side portion 11 and clamps these free ends towards each other. Thereby a uniform pulling force is exerted over the entire periphery of the cheek-side portion which later will be reliably fixed by hardened material in the groove 15.

Figure 6:
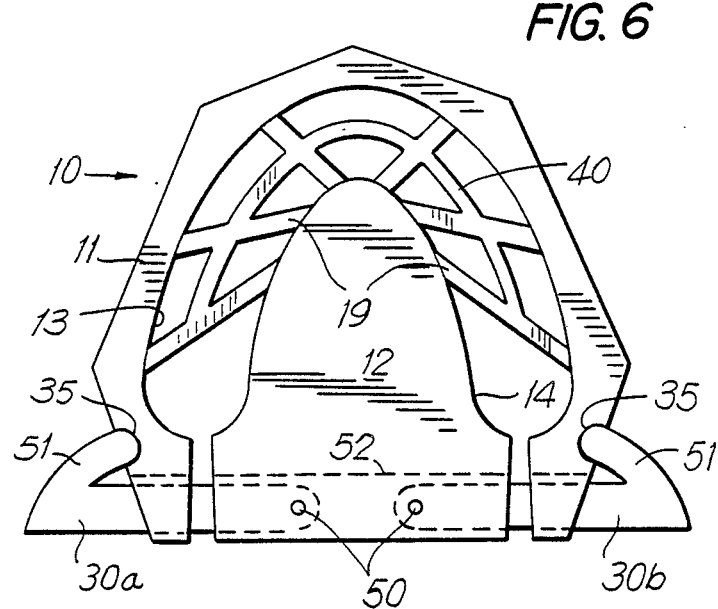
FIG. 6 is a plan view of the base plate of a second embodiment.

FIG. 6 shows another embodiment of the base plate 10 with a different version of webs 19. Some webs 19 are connected to each other by a reinforcing web 40 extending to the middle along the groove 15. In addition, two clamps or clasps 30a, 30b are provided which clamp the free ends of the cheek-side plate portion 11 relative to the tongue-side plate portion. Both clasps 30a, 30b are pivotable on hinge axes 50 provided on the tongue-side plate portion 12 and can engage with boom-like projections 51 of the cheek-side plate portion 11 and yield into locking recesses 35 Thereby a guide groove 52 is formed at the backside of the plate. The height of groove 52 corresponds to the thickness of clasps 30a, 30b. Due to cooperation of the clasps 30a, 30b and the guide groove 52, the two-side orientation of both plate portions 11 and 12 transversely to the base surfaces, and additionally a reinforcement of these elements are ensured.

Both clasps 30a, 30b can, of course, be pivoted on their hinge axes. Thus a non-releaseable or lockable pivoting is possible whereby each clasp carries a hinge axis which is insertable and lockable in the locking recess provided on the tongue-side plate portion. Such a double clamping can be also formed by a single element in which two clasps would be connected to each other by the film hinge.

Figure 7:
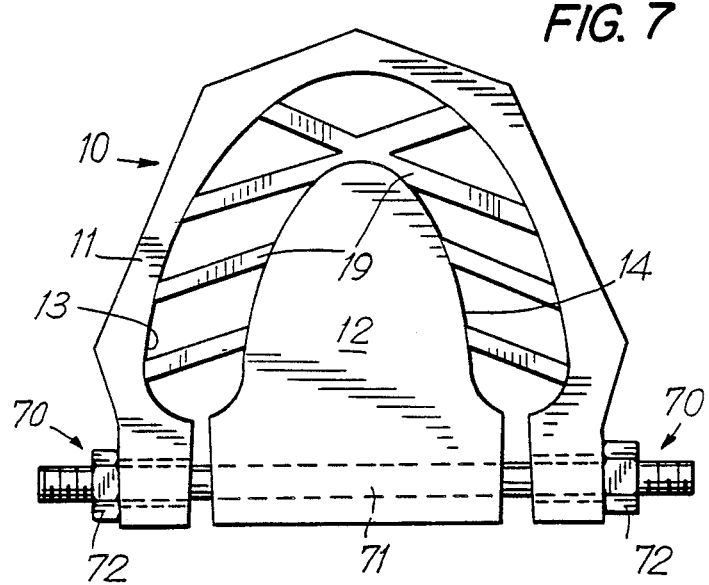
FIG. 7 is a plan view of the base plate of a third embodiment.

FIG. 7 shows yet another embodiment of the invention. In this embodiment, in place of the clasp, a bolt connection 70 for locking the plate portions to each other is suggested. Parallel to the back surface of the base plate 10 are formed aligned bores in both plate portions 11 and 12. A pin 71 provided with a thread at its end penetrates the bore formed in the tongue-side plate portion 12 and is pressed in the bores formed in the free ends of the cheek-side portion 11. At both end sides of the threaded pin 71, nuts 72 can be screwed whereby the free ends of the cheek-side plate portion 11 can be clamped individually relative to the tongue-side plate portion 12. In place of the single through pin, two pins can be, certainly, utilized, which pins would be pressed into the bores of plate portion 12 from the sides of this portion. With the one-piece pin a press fit in the tongue-side plate portion is not necessary because the free ends of the plate portion 11 can be also clamped to each other.

The threaded pin and nuts are, as well as clasps, formed of plastic, for example polyamide; however these structural components can be made of metal with resilient properties. It is substantial that these locking parts could have certain allowances with various strong expansions. This can be obtained by the elasticity of the utilized material or by a suitable structure of the locking connection itself. The tolerance compensation with the screw connection is possible by various tightening of the nuts.

The remaining figures of the drawings illustrate yet a further embodiment of the invention. In this embodiment, each web 19 has such a shape that it has a reduced cross-section in the middle portion 20a. With such structure of the webs, a required translatory and rotation movement of the cheek-side side wall 13 or plate portion 11 is ensured in the optimal way.

Figure 12:
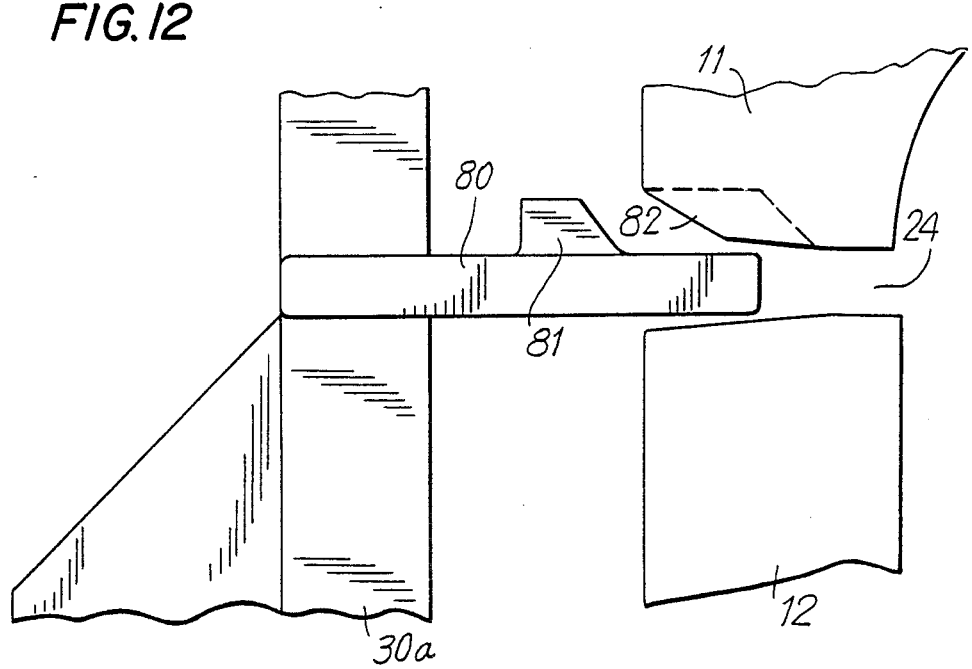
FIG. 12 shows a clasp, on enlarged scale.
Figure 13:
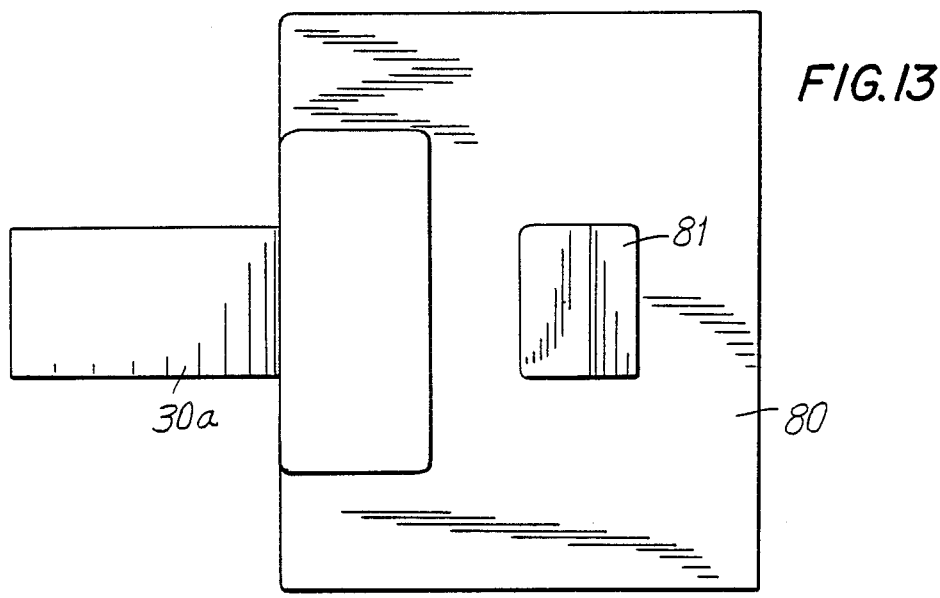
FIG. 13 is a side view of the clasp of FIG. 12.

Specifically important is the structure of clasps 30a and 30b. With reference to FIG. 8 it will be seen that these clasps are guided firstly into the grooves 52 of the tongue-side plate portion 12, in which they are pivotally lockable by means of hinge axes 50. At the portion of clasp 30a laterally extending from the groove 52, is formed a plate 80 extending at right angles to clasp 30a, as shown in FIGS. 12 and 13. Plate 80 carries a projection 81 which can be inserted into a recess 82 provided in the cheek-side plate portion 11. This recess or groove 82 extends parallel to the base surface of the base plate. In this fashion, the alignment of both base plate portions in the direction transversal to the base surface is ensured. Plate 80 fills the play 24 between the base plate portions 11 and 12 and thus closes groove 15 in the circumferential direction so that no model material can expand outwards.

As shown in FIG. 8, each clasp 30a, 30b has a projection, preferably resilient abutment 84 which, after the assembling of the clasp in the longitudinal direction and the following pivoting to the operation position, makes the pivoting of the clasp back to the assembly position difficult. This abutment 84 strikes against a wall 85 of the partially hollow base plate, and the clasp can no longer pivot back in the direction of arrow P and thus no longer be released from the base portion 12 without the application of a substantial force.

FIG. 10 depicts, on enlarged scale, the design of retention means which are projections 16 formed on the cheek-side wall 13. As seen from the drawing, each two wall portions 90, 91 which form one projection 16a on the cheek-side wall 13 include with the normal line N to the side wall uneven angles W1 and W2. Angle W2 between the normal line N and the wall portion 90 aligned with the jaw teeth area is greater than angle W1. which defined between the other wall portion 91 of projection 16a and the normal line N. Angle W2 lies in the range between 50 and 70 deg., preferably 50 degrees whereas smaller angle W1 is in the range between 25 and 35 degrees, preferably 30 deg. Since the direction of the normal line changes the shape or the alignment of projections 16 along the side wall 13 also changes. The projections on the internal, e.g. tongue-side wall 14 have the wall portions which are substantially symmetrical to the normal. This means that the shape of the cross-section of projection 16a on the side wall 13 of the cheek-side base plate portion 11 differs from the cross-section of projection 16b on the wall 14 of the tongue-side base plate portion 12 at least partially.

It is of course understandable that extensions of the webs in two different points in the middle plane are also conceivable in the embodiment of FIGS. 8–10. This dimensioning of the cross-sections of the webs is adjusted to the distribution along the dental arch and the place and the length of the cross-section reduction, and desired moving results are obtained. Finally the shapes of the cross-sections of the ribs or projections 16 are also adjusted.

Further non-shown modifications of the base plate according to the invention are also possible. The webs could for example, extend, at least partially parallel to each other. The central point of all webs could lie in the region of the groove or be upwardly offset from that in the embodiment of FIG. 1. The webs could be also made of a suitable resilient material, even metal. The webs could, for example, bridge the groove in a zigzag manner. Only a small number of the webs are shown in the drawings for the sake of clarity, such a number of the webs could be provided that these webs would cover preferably the half of the base surface of the groove. Thereby stability of the base plate in substantially enhanced. The webs could also lie within the lower base surface of two base plate portions. In a preferable embodiment, the webs could be immersed in the hardenable model material and thus additionally contribute to the guidance and positioning of individual tooth stumps. By the insertion of the film or foil which would form the base surface of the groove, it would be ensured that the model material would not flow between the webs and influence their flexibility.

Only those embodiments are shown in the drawings, in which the cheek-side plate portion is formed of one-piece. This plate portion can be also multi-part, particularly in the front teeth area. Then the clasps could be also applied from the front teeth area. Instead of the clasps, could be utilized a clamping tape guided in the groove. Such a tape would be preferable specifically with a multi-part cheek-side base plate portion.

The entire base plate is preferably injection-molded from plastic. This plate can be formed of mineral glass.

During the injection-molding of the base plate possible uniform wall reinforcements can be made.

Of course, so-called splitcast ribs can be provided in the known fashion on the base plate, which ribs extend radially outwardly from the middle point. A bore for a pin of a magnetic disc could be provided in the middle point.

The process of producing denture models is as follows:

The base plate is adjusted in the plane lower position or locked from below, for example with a self-adhesive film. Then the groove is filled with a model material, preferably gypsum. Such dental impression filled with gypsum is turned over on the base plate and is aligned thereon. The portions of the base plate can be locked with each other. As soon as the gypsum is hardened which takes about 15–20 minutes, the locking connection is released. The model material expands only during the duration of hardening whereby the shape of the base plate fits this expansion. Then the denture model arch is removed from the base plate and is sawn off whereby a linear expansion is absorbed in the direction of elongation of the dental arch. It is possible to divide the dental arch into a number of individual segments, also when not all the model stumps should be prepared. Individual tooth stumps can then be placed back into the groove of the base plate and the base plate or its portion will be locked with each other. Finally, the model is treated in the usual fashion, for which it is clamped in an articulator.

The method of making dental models can be executed in such a manner that the locking of the base plate portions would be conducted right after the gypsum hardening or returning of the tooth stumps into the base plate.

A significant advantage of the invention is the fact that it is quickly assembled. Due to a possible deflection of the side walls or the base plate portion, the plate can be adjusted to an unvoidable expansion of the model material. Due to a later locking or blocking of the base plate portions, sufficient stability of the base plate is ensured. Slight displacements of the base plate portions are compensated by guidance. Such a compensation also takes place for tilting and rotation motions of the cheek-side base plate portion, which motions are not completely avoided. Also, errors in a height relation of individual tooth stumps, which occur in use of conventional base plates are avoided with the base plate according to the invention. Due to this invention an absolute precision in the production of dental models, particularly when the gypsum is utilized, is obtained. The base plate can also be used for dental models of plastics with which expansion is not so noticeable.

It will be understood that each of the elements described above, or two or more together, may also find a useful application in other types of supporting plates differing from the types described above.

While the invention has been illustrated and described as embodied in a supporting plate, it is not intended to be limited to the details shown, since carious modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic of specific aspects of this invention.

What is claimed as new and desired to be protected by Letters Patent is set forth in the appended claims.

1. A supporting plate for a dental model for preparation of dental prothesis parts, comprising a first tongue-side portion and a second cheek-side portion both having side walls which are to be aligned with each other, said first and second portions defining therebetween a groove of a shape corresponding to the shape of a tooth arch and forming respective guiding surfaces for the guiding a model tooth stump during the hardening of a model material, and means including a plurality of connection elements (19) for holding said second portion to said first portion and at the same time permitting uniform movement between opposite sides of said first and second portions so as to permit a change in a distance between a side wall (13) of said second portion and a side wall (14) of said first portion.

2. The supporting plate as defined in claim 1, wherein said connection element include means for elastically counteracting an increase of said distance between side walls of said second and first portion.

3. The supporting plate as defined in claim 2, wherein a space (25) is provided to assume the smallest distance (A) between said side walls (13,14).

4. The supporting plate as defined in claim 3, wherein said connection element (19) acts as a spacer element.

5. The supporting plate as defined in claim 4, wherein a plurality of connection elements are provided which are formed by webs (19), said webs being parallel to each other.

6. The supporting plate as defined in claim 4, wherein a plurality of connection elements are provided which are formed as elastic webs in a direction of elongation thereof and also in a direction transversal to said groove.

7. The supporting plate as defined in claim 1, wherein said connecting element is formed by a web and is pivotable by an angle deviated from 90° on a side wall of each portion.

8. The supporting plate as defined in claim 7, wherein said web includes integral hinges (20) connected to the side wall of each portion.

9. The supporting plate as defined in claim 8, wherein a plurality of connection elements are provided, said connection elements being formed by webs which are spaced from each other.

10. The supporting plate as defined in claim 7, wherein said web is formed of one-piece with said first and second portion and has an intermediate portion positioned in the middle between said second and first position, said intermediate portion (20a) having a reduced cross-section.

11. The supporting plate as defined in claim 10 wherein a plurality of connection elements are provided, said connection from each other.

12. The supporting plate as defined in claim 7, wherein a plurality of connection elements are provided, said connection elements being formed by webs which are spaced from each other.

13. The supporting plate as defined in claim 12, wherein at least said webs are connected to each other by a reinforcing web (40) extending in the middle between said second and first portion along said groove.

14. The supporting plate as defined in claim 12, wherein said webs cover more than one half of a base area of said groove.

15. The supporting plate as defined in claim 12, wherein said webs are positioned in the region of lower base surfaces (22) of said first and second portion.

16. The supporting plate as defined in claim 15, wherein said webs are flush with said lower base surfaces.

17. The supporting as defined in claim 16, wherein a thin foil which closes said groove before said groove is filled with model material, is placed on said webs, said foil forming said base surfaces.

18. The supporting plate as defined in claim 15, wherein said webs lie within a plane of said lower base surfaces (22).

19. The supporting plate as defined in claim 1, further including locking means for elastically locking said first portion with said second portion with a sufficient clamping force.

20. The supporting plate as defined in claim 19, wherein said locking means include at least one clasp which clamps free ends of said second portion with said first portion.

21. The supporting plate as defined in claim 20, wherein said clasp (30) has two bridges (31,32) and a cross-piece (34 connecting said bridges to each other, said bridges engaging opposite base surfaces of said first and second portion and snugly closing said first and second portion.

22. The supporting plate as defined in claim 20, wherein said clasp (30) has two bridges (31,32), and locking pins (33) connecting said bridges to each other, said bridges engaging opposite base surfaces of said first and second portion and snugly closing said first and second portion.

23. The supporting plate as defined in claim 19, wherein said locking means include two clasps(30a, 30b) which clamp free ends of said second portion with said first portion, said two clasps being pivotally connected to each other.

24. The supporting plate as defined in claim 23, wherein said clasps are locked in one of said portions.

25. The supporting plate as defined in claim 24, wherein said clasps are locked in said first portion.

26. The supporting plate as defined in claim 23, wherein at least one of said portions has a recess (52) in which said two clasps (30a, 30b) are engaged.

27. The supporting plate as defined in claim 26, wherein said first portion (12) has said recess (52) in which said two clasps are engaged, said clasps being supported in said second portion (11).

28. The supporting plate as defined in claim 26, each clasp having a projection (81) which is engaged in a recess (82) formed in a respective one of said portions.

29. The supporting plate as defined in claim 28, each clasp having a plate portion (80) provided with said projection (81), said plate extending substantially normal to elongation of said clasp and projecting into a play (24) between said first and second portion and filling said play.

30. The supporting plate as defined in claim 28, wherein each clasp further has a resilient abutment (84) which, after the assembly of the clasp in a direction of elongation and a following pivoting to an operation position, makes a pivoting of the clasp backward to an assembly position difficult.

31. The supporting plate as defined in claim 19, wherein said locking means include a bolt connection (70) which connects free ends of said second portion to said first portion.

32. The supporting plate as defined in claim 19, wherein said locking means include two clasps which clamp free ends of said second portion and are pivotally connected to said first portion (12).

33. The supporting plate as defined in claim 19, wherein said locking means includes a tub-shaped mold into which the supporting plate is directly insertable so that an outer wall of said second portion lies against a side wall of the mold.

34. The supporting plate as defined in claim 1, wherein side walls of said first and second portion, which face towards each other have ribs (16), wherein a cross-section of each rib (16a) on a side wall of said second portion differs from a cross-section of each rib (16b) on a side wall of said first portion, each rib (16a) having wall portions (90,91) which include with a normal (N) to the side wall of said second portion a different angle ($W_1$, $W_2$), and an angle $W_2$ between said normal and a wall portion (90) directed towards a back teeth region being greater than an angle ($W_1$) between said normal and a wall portion (91).

35. The supporting plate as defined in claim 34, wherein angle ($W_2$) is in the range between 50 and 60 deg. and angle ($W_1$) is in the range between 25 and 35 deg.

36. The supporting plate as defined in claim 35, wherein said angle ($W_2$) is 60°.

37. The supporting plate as defined in claim 35, wherein said angle ($W_1$) is 30°.

38. The supporting plate as defined in claim 1, wherein said plate is made of plastic.

39. The supporting plate as defined in claim 1, said plate being made of mineral glass.

40. The supporting plate as defined in claim 1, wherein said side wall of said first portion and said side wall of said second portion are directed parallel to each other so that a conventional sloped shape necessary for a tip is disposed of.

41. A method of making a dental model by means of a mold with a supporting plate comprising a first tongue-side portion and a second cheek-side portion both having side walls which are to be aligned with each other, said first and second portion defining therebetween a groove of a shape corresponding to the shape of a tooth arch and forming respective guiding surfaces for guiding a model tooth stump during the hardening of a model material, and at least one connection element (19) for holding said second portion to said first portion, said connection element being formed so that it permits a change in a distance between a side wall (13) of said second portion and a side wall (14) of said first portion, the method comprising the steps of filling a hardenable model material into said supporting plate, the side walls of which during hardening of said material form guide surfaces on a guide abutment of a model tooth stump, wherein at least during a predetermined time interval while said material is hardened, a deflection of a side wall of a portion of the supported plate is permitted.

42. The method as defined in claim 41, comprising the step of locking said first portion to said second portion only for making a dental prothesis portion.

43. The method as defined in claim 38, comprising the steps of locking said first and second portion to each other before said material is filled thereinto, and releasing said first portion after said material has been solidified.

44. The method as defined in claim 43, wherein a dental model after solidifying of said material is removed from the supporting plate for hardening of said material.

45. The supporting plate as defined in claim 1, wherein said connection element is a flexible connection element, said connection element acting as a hinge so that it permits a change in a distance between a side wall (13) of said second portion and a side wall (14) in said first portion.

* * * * *